United States Patent [19]

Brazdil, Jr. et al.

[11] Patent Number: 5,994,259

[45] Date of Patent: Nov. 30, 1999

[54] CATALYSTS FOR THE AMMOXIDATION OF ALKANES

[75] Inventors: James Frank Brazdil, Jr.; Joseph Peter Bartek, both of Highland Heights, Ohio

[73] Assignee: The Standard Oil Company, Chicago, Ill.

[21] Appl. No.: 09/124,956

[22] Filed: Jul. 29, 1998

[51] Int. Cl.[6] .............................. B01J 23/00; B01J 23/58; B01J 23/16

[52] U.S. Cl. .................. 502/300; 502/325; 502/328; 502/349; 502/350; 502/352; 502/353

[58] Field of Search .................................. 502/325, 338, 502/300, 349, 350, 352, 353

[56] References Cited

U.S. PATENT DOCUMENTS

| | | | |
|---|---|---|---|
| 3,686,267 | 8/1972 | Taylor | 260/465.3 |
| 4,162,992 | 7/1979 | Wise | 252/456 |
| 4,388,248 | 6/1983 | Wise | 260/465.3 |
| 5,008,427 | 4/1991 | Brazdil, Jr. et al. | 558/319 |
| 5,231,214 | 7/1993 | Ushikubo et al. | 558/319 |
| 5,432,141 | 7/1995 | Brazdil, Jr. et al. | 502/312 |
| 5,470,815 | 11/1995 | Kim et al. | 502/317 |
| 5,675,057 | 10/1997 | Bremer et al. | 502/352 |
| 5,686,381 | 11/1997 | Albonetti et al. | 502/352 |
| 5,854,172 | 12/1998 | Brazdil, Jr. et al. | 502/352 |

*Primary Examiner*—Mark L. Bell
*Assistant Examiner*—Patricia L. Hailey
*Attorney, Agent, or Firm*—David P. Yusko; Wallace L. Oliver

[57] ABSTRACT

An ammoxidation catalyst characterized by the following empirical formula comprising:

$$VSb_aSn_bTi_cFe_dO_x$$

where $1 \leq a \leq 1.8$ $0 \leq b \leq 0.35$ $0 \leq c \leq 0.15$ $0 < d \leq 0.8$ $0 < b+c \leq 0.5$ $1 \leq a-d < 1.8$ and when $a-d > 1.2$ then $0 < d < 0.5$ and $0.3 \leq b+c \leq 0.5$ and when $a-d \leq 1.2$ then $0.2 < d \leq 0.8$ and $0 < b+c < 0.3$ and x is determined by the oxidation states of the cations present in the catalyst.

Preferably, the catalyst has been calcined at a temperature of at least 780° C.

16 Claims, No Drawings

CATALYSTS FOR THE AMMOXIDATION OF ALKANES

BACKGROUND OF THE INVENTION

Field of the Invention

The present invention is directed to a catalyst and a process for the catalytic ammoxidation of propane and isobutane to their corresponding $\alpha,\beta$-unsaturated mononitriles; i.e., acrylonitrile and methacrylonitrile, utilizing the disclosed catalyst.

Because of the price differential between propylene and propane, an economic incentive exists for the development of a viable catalyst and catalytic process for the conversion of propane to acrylonitrile.

Earlier attempts in the prior art to develop an efficient process for the ammoxidation of propane to acrylonitrile produced either insufficient yields or processes that necessitated adding halogen promoters to the feed. The latter procedure would require not only reactors made of special corrosion-resistant materials, but also a quantitative recovery of the promoter. The added costs thus eliminated the advantages of the propane/propylene price differential.

Recently, U.S. Pat. Nos. 5,008,427 and 5,498,588 assigned to the assignee of the instant application have been directed to novel propane ammoxidation catalysts and the process of utilizing these catalysts to produce acrylonitrile from propane. The present invention is directed to improvements in these catalysts.

SUMMARY OF THE INVENTION

It is the object of the present invention to provide an improved catalyst for the ammoxidation of paraffins to unsaturated mononitriles, in particular, the ammoxidation of propane and isobutane to acrylonitrile or methacrylonitrile.

It is a further object of the present invention to provide an improved catalytic ammoxidation process for making unsaturated mononitriles from lower paraffins, in particular, the catalytic ammoxidation process for the production of acrylonitrile and methacrylonitrile from propane and isobutane, respectively.

Other objects as well as aspects, features and advantages of the present invention will become apparent from the study of the accompanying disclosure and the appended claims.

According to one aspect of the invention, there is provided a catalyst comprising the elements in proportions indicated by the following empirical formula:

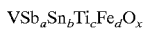

where
$1 \leq a \leq 1.8$
$0 \leq b \leq 0.35$
$0 \leq c \leq 0.15$
$0 < d \leq 0.8$
$0 < b+c \leq 0.5$
$1 \leq a-d < 1.8$
and when $a-d > 1.2$
then $0 < d < 0.5$ and $0.3 \leq b+c \leq 0.5$
and when $a-d \leq 1.2$
then $0.2 < d \leq 0.8$ and $0 < b+c < 0.3$
and x is determined by the oxidation states of the cations present in the catalyst.

In another aspect of the present invention, a process for making an $\alpha,\beta$-unsaturated mononitrile comprises contacting in a reaction zone in the vapor phase a paraffin selected from the group consisting of propane and isobutane with oxygen and ammonia in the presence of a catalyst, the gaseous composition in the reaction zone containing a mole ratio of paraffin to ammonia in the range of from 2.5 to 16 and a mole ratio of paraffin to oxygen in the range of from about 1 to 10, said catalyst having the elements and proportions indicated by the empirical formula:

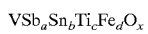

where
$1 \leq a \leq 1.8$
$0 \leq b \leq 0.35$
$0 \leq c \leq 0.15$
$0 < d \leq 0.8$
$0 < b+c \leq 0.5$
$1 \leq a-d < 1.8$
and when $a-d > 1.2$
then $0 < d < 0.5$ and $0.3 \leq b+c \leq 0.5$
and when $a-d \leq 1.2$
then $0.2 < d \leq 0.8$ and $0 < b+c < 0.3$
and x is determined by the oxidation states of the cations present in the catalyst.

In a further preferred embodiment of the present invention, the catalyst comprises the elements in proportions indicated by the following empirical formula:

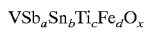

where
$1.3 \leq a \leq 1.8$
$0 \leq b \leq 0.2$
$0 \leq c \leq 0.1$
$0.2 < d \leq 0.6$
$0 < b+c < 0.3$
$1 \leq a-d \leq 1.2$
and x is determined by the oxidation states of the cations present in the catalyst.

In a further preferred embodiment of the present invention the catalyst comprises the elements in proportions indicated by the following empirical formula:

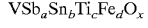

where
$1.5 \leq a \leq 1.8$
$0 \leq b \leq 0.1$
$0 \leq c \leq 0.05$
$0.3 \leq d \leq 0.6$
$0 < b+c \leq 0.15$
$1 \leq a-d \leq 1.2$
and x is determined by the oxidation states of the cations present in the catalyst.

In still another preferred embodiment of the present invention, the calcination temperature for the preparation of the catalyst is at least 780° C. Calcination temperatures as high as 1200° C. may be utilized. However, calcination temperatures usually in the range of 790° to 1050° C. are preferred. The optimum calcination temperature can vary from composition to composition, but the particular narrow optimum calcination temperature range for a given composition can be determined easily by routine experimentation.

In the ammoxidation process of the present invention, the reaction is carried out in the gaseous phase by contacting a mixture of the paraffin, ammonia and molecular oxygen in the reaction zone. In addition, an inert diluent such as nitrogen, helium, carbon dioxide and water may be utilized in the practice of the invention.

The reaction temperature range can vary from 350° to 700° C. but is usually between 430° to 520° C. The latter temperature is especially useful in the case of propane ammoxidation to acrylonitrile.

The average contact time during the process can often be from 0.01 to 10 seconds, but is usually from 0.02 to 10 seconds, most preferably between 0.1 to 5 seconds.

The pressure in the reaction zone usually ranges from 2 to 75 psia, most preferably, from 2 to up to 50 psia.

For specific details as to the catalyst preparation preferred in the practice of the present invention, reference is made to U.S. Pat. No. 5,008,427, assigned to the assignee of the present application and herein incorporated by reference.

DETAILED DESCRIPTION OF THE INVENTION

The catalyst and process of the present invention are herein set forth in further detail. The examples are presented for illustration purposes only and are not considered limiting.

EXAMPLES OF THE INVENTION

TABLE I

| Example No. | Catalyst Composition | WWH (hr$^{-1}$) | Temp. (° C.) | Pressure (psig) | Feed Ratios C3H8 | NH3 | O2 | N2 | C3H8 Conv. (%) | Acrylonitrile Selectivity (%) |
|---|---|---|---|---|---|---|---|---|---|---|
| 1 | VSb 1.5 Sn .05 Ti .05 Fe .035 Ox + 20% SiO2 | 0.82 | 480 | 15 | 3.00 | 0.79 | 2.01 | 2.00 | 20.29 | 59.14 |
| 2 | VSb 1.6 Sn .02 Ti .04 Fe .6 Ox + 20% SiO2 | 1.60 | 480 | 15 | 3.00 | 0.81 | 2.00 | 1.99 | 20.17 | 58.35 |
| 3 | VSb 1.8 Sn .05 Ti .05 Fe .6 Ox + 20% SiO2 | 1.23 | 480 | 15 | 3.00 | 0.79 | 2.00 | 2.01 | 20.63 | 57.86 |
| 4 | VSb 1.61 Sn .05 Ti .05 Fe .6 Ox + 20% SiO2 | 1.36 | 480 | 15 | 3.00 | 0.80 | 1.99 | 1.99 | 20.57 | 57.42 |
| 5 | VSb 1.38 Sn .05 Ti .1 Fe .3 Ox + 20% SiO2 | 0.94 | 475 | 15 | 3.00 | 0.79 | 2.00 | 2.01 | 19.91 | 57.33 |
| 6 | VSb 1.6 Sn .02 Ti .02 Fe .5 Ox + 20% SiO2 | 1.62 | 480 | 15 | 3.00 | 0.81 | 2.00 | 1.99 | 20.14 | 57.28 |
| 7 | VSb 1.5 Sn .2 Ti .1 Fe .1 Ox + 20% SiO2 | 1.46 | 480 | 15 | 3.00 | 0.79 | 2.00 | 2.01 | 20.07 | 57.19 |
| 8 | VSb 1.38 Sn .05 Ti .1 Fe .3 Ox + 20% SiO2 | 1.07 | 480 | 15 | 3.00 | 0.79 | 2.00 | 2.01 | 20.27 | 57.16 |
| 9 | VSb 1.4 Ti .15 Fe .35 Ox + 20% SiO2 | 1.05 | 480 | 15 | 3.00 | 0.79 | 2.01 | 2.00 | 20.66 | 56.86 |
| 10 | VSb 1.5 Sn 0.05 Ti 0.1 Fe 0.35 Ox + 20% SiO2 | 0.84 | 475 | 15 | 3.00 | 0.81 | 1.97 | 2.01 | 19.54 | 56.08 |
| 11 | VSb 1.4 Ti .15 Fe .35 Ox + 20% SiO2 | 1.05 | 475 | 15 | 3.00 | 0.79 | 2.01 | 2.00 | 19.65 | 56.05 |

COMPARATIVE EXAMPLES

TABLE II

| Comp. Example No. | Catalyst Composition | WWH (hr$^{-1}$) | Temp. (° C.) | Pressure (psig) | Feed Ratios C3H8 | NH3 | O2 | N2 | C3H8 Conv. (%) | Acrylonitrile Selectivity (%) |
|---|---|---|---|---|---|---|---|---|---|---|
| 12 | VSb 1.38 Ti .1 Fe .1 Ox + 20% SiO2 | 0.48 | 485 | 15 | 3.00 | 0.79 | 2.00 | 2.01 | 20.19 | 55.75 |
| 13 | VSb 1.2 Sn 0.05 Ti .15 Fe 0.1 Ox + 20% SiO2 | 0.67 | 480 | 15 | 3.00 | 0.80 | 1.96 | 2.06 | 19.59 | 55.70 |
| 14 | VSb 1.3 Ti .15 Fe 0.2 Ox + 20% SiO2 | 0.59 | 480 | 15 | 3.00 | 0.80 | 2.01 | 2.00 | 19.61 | 54.33 |
| 15 | VSb 1.6 Fe 0.5 Ox + 20% SiO2 | 0.67 | 480 | 15 | 3.00 | 1.02 | 2.02 | 1.99 | 20.10 | 53.80 |
| 16 | VSb 1.8 Sn 0.05 Ti 0.15 Fe 0.1 Ox + 20% SiO2 | 0.37 | 480 | 15 | 3.00 | 0.81 | 1.96 | 2.02 | 20.24 | 53.42 |

The following table provides additional examples of the invention and comparative examples. The "C" in front of the Example No. denotes a "comparative" example.

TABLE III

| Example No. | Catalyst Composition | WWH (hr$^{-1}$) | Temp. (° C.) | Pressure (psig) | Feed Ratios C3H8 | NH3 | O2 | N2 | C3H8 Conv. (%) | Acrylonitrile Selectivity (%) |
|---|---|---|---|---|---|---|---|---|---|---|
| 17 | VSb 1.5 Sn .05 Ti .05 Fe .35 Ox + 20% SiO2 | 0.82 | 480 | 15 | 3.00 | 0.79 | 2.01 | 2.00 | 20.29 | 55.14 |
| 18 | VSb 1.5 Sn .05 Ti .15 Fe .35 Ox + 20% SiO2 | 0.76 | 480 | 15 | 3.00 | 0.79 | 2.01 | 2.00 | 21.38 | 59.06 |
| 19 | VSb 1.6 Sn .02 Ti .04 Fe .6 Ox + 20% SiO2 | 1.60 | 480 | 15 | 3.00 | 0.81 | 2.00 | 1.99 | 20.17 | 58.35 |
| 20 | VSb 1.38 Ti .1 Fe .3 Ox + 20% SiO2 | 0.70 | 480 | 15 | 3.00 | 0.79 | 2.00 | 2.01 | 20.17 | 58.21 |
| C21 | VSb 1.5 Sn .125 Ti .05 Fe .225 Ox + 20% SiO2 | 0.67 | 480 | 15 | 3.00 | 0.81 | 2.00 | 1.99 | 20.81 | 57.99 |
| C22 | VSb 1.2 Sn 0.05 Ti 0.05 Fe 0.1 Ox + 20% SiO2 | 0.53 | 480 | 15 | 3.00 | 0.80 | 1.97 | 2.09 | 19.64 | 57.89 |
| 23 | VSb 1.8 Sn .05 Ti .05 Fe .6 Ox + 20% SiO2 | 1.23 | 480 | 15 | 3.00 | 0.79 | 2.00 | 2.01 | 20.63 | 57.86 |
| C24 | VSb 1.38 Ti .1 Fe .2 Ox + 20% SiO2 | 0.66 | 485 | 15 | 3.00 | 0.79 | 2.00 | 2.01 | 20.14 | 57.85 |
| 25 | VSb 1.61 Sn .05 Ti .05 Fe .6 Ox + 20% SiO2 | 1.36 | 480 | 15 | 3.00 | 0.80 | 1.99 | 1.99 | 20.57 | 57.42 |

TABLE III-continued

| Example No. | Catalyst Composition | WWH (hr$^{-1}$) | Temp. (° C.) | Pressure (psig) | Feed Ratios C3H8 | NH3 | O2 | N2 | C3H8 Conv. (%) | Acrylonitrile Selectivity (%) |
|---|---|---|---|---|---|---|---|---|---|---|
| 26 | VSb 1.38 Sn .05 Ti .1 Fe .3 Ox + 20% SiO2 | 0.94 | 475 | 15 | 3.00 | 0.79 | 2.00 | 2.01 | 19.91 | 57.33 |
| 27 | VSb 1.6 Sn .02 Ti .02 Fe .5 Ox + 20% SiO2 | 1.62 | 480 | 15 | 3.00 | 0.81 | 2.00 | 1.99 | 20.14 | 57.28 |
| 28 | VSb 1.5 Sn .2 Ti .5 Fe .1 Ox + 20% SiO2 | 1.46 | 480 | 15 | 3.00 | 0.79 | 2.00 | 2.01 | 20.07 | 57.19 |
| 29 | VSb 1.38 Sn .05 Ti .1 Fe .3 Ox + 20% SiO2 | 1.07 | 480 | 15 | 3.00 | 0.79 | 2.00 | 2.01 | 20.27 | 57.16 |
| C30 | VSb 1.2 Sn .35 Ti .05 Fe .1 Ox + 20% SiO2 | 1.71 | 480 | 15 | 3.00 | 0.79 | 2.00 | 2.00 | 20.13 | 56.94 |
| C31 | VSb 1.5 Sn .125 Ti .05 Fe .225 Ox + 20% SiO2 | 0.68 | 480 | 15 | 3.00 | 0.81 | 2.00 | 1.99 | 20.57 | 56.86 |
| 32 | VSb 1.4 Ti .15 Fe .35 Ox + 20% SiO2 | 1.05 | 480 | 15 | 3.00 | 0.79 | 2.01 | 2.00 | 20.66 | 56.86 |
| C33 | VSb 1.38 Sn .05 Ti .1 Fe .2 Ox + 20% SiO2 | 0.64 | 485 | 15 | 3.00 | 0.79 | 2.00 | 2.01 | 20.23 | 56.79 |
| C34 | VSb 1.38 Sn .05 Ti .1 Fe .1 Ox + 20% SiO2 | 0.47 | 485 | 15 | 3.00 | 0.79 | 2.00 | 2.01 | 19.58 | 56.27 |
| 35 | VSb 1.5 Sn 0.05 Ti 0.15 Fe 0.35 Ox + 20% SiO2 | 0.68 | 480 | 15 | 3.00 | 0.80 | 1.96 | 2.06 | 19.84 | 56.17 |
| 36 | VSb 1.5 Sn 0.05 Ti 0.1 Fe 0.35 Ox + 20% SiO2 | 0.84 | 475 | 15 | 3.00 | 0.81 | 1.97 | 2.01 | 19.54 | 56.08 |
| 37 | VSb 1.4 Ti .15 Fe .35 Ox + 20% SiO2 | 1.05 | 475 | 15 | 3.00 | 0.79 | 2.01 | 2.00 | 19.65 | 56.05 |
| C38 | VSb 1.38 Ti .1 Fe .1 Ox + 20% SiO2 | 0.48 | 485 | 15 | 3.00 | 0.79 | 2.00 | 2.01 | 20.19 | 55.75 |
| C39 | VSb 1.2 Sn 0.05 Ti 0.15 Fe 0.1 Ox + 20% SiO2 | 0.67 | 480 | 15 | 3.00 | 0.80 | 1.96 | 2.06 | 19.59 | 55.70 |
| 40 | VSb 1.5 Sn 0.05 Ti 0.1 Fe 0.35 Ox + 20% SiO2 | 0.84 | 480 | 15 | 3.00 | 0.81 | 1.97 | 2.01 | 20.78 | 55.65 |
| C41 | VSb 1.5 Sn .35 Ti .1 Fe .35 Ox + 20% SiO2 | 1.71 | 480 | 15 | 3.00 | 0.79 | 2.00 | 2.00 | 19.96 | 55.58 |
| C42 | VSb 1.2 Sn .35 Ti .15 Fe .1 Ox + 20% SiO2 | 1.79 | 480 | 15 | 3.00 | 0.79 | 2.00 | 2.00 | 20.04 | 55.39 |
| 43 | V 1.0 Sb 1.5 Sn 0.2 Ti 0.05 Fe 0.35 Ox + 20% SiO2 | 1.30 | 480 | 15 | 3.00 | 0.82 | 1.97 | 2.04 | 20.96 | 55.35 |
| C44 | VSb 1.8 Sn .04 Ti .02 Fe .5 Ox + 20% SiO2 | 1.56 | 480 | 15 | 3.00 | 0.81 | 2.00 | 1.99 | 20.29 | 54.92 |
| 45 | VSb 1.8 Sn .02 Ti .02 Fe .6 Ox + 20% SiO2 | 1.28 | 480 | 15 | 3.00 | 0.82 | 2.01 | 2.00 | 20.09 | 54.81 |
| C46 | VSb 1.3 Ti .15 Fe .2 Ox + 20% SiO2 | 0.59 | 480 | 15 | 3.00 | 0.80 | 2.01 | 2.00 | 19.61 | 54.33 |
| C47 | VSb 1.5 Sn 0.2 Ti 0.15 Fe 0.35 Ox + 20% SiO2 | 1.29 | 480 | 15 | 3.00 | 0.82 | 1.97 | 2.04 | 19.99 | 54.00 |
| C48 | VSb 1.5 Sn .125 Ti .05 Fe .1 Ox + 20% SiO2 | 0.45 | 480 | 15 | 3.00 | 0.80 | 1.99 | 1.99 | 20.51 | 53.83 |
| C49 | VSb 1.6 Fe 0.5 Ox + 20% SiO2 | 0.67 | 480 | 15 | 3.00 | 1.02 | 2.02 | 1.99 | 20.10 | 53.80 |
| C50 | VSb 1.8 Sn .35 Ti .15 Fe .1 Ox + 20% SiO2 | 1.26 | 480 | 15 | 3.00 | 0.79 | 2.00 | 2.00 | 19.50 | 53.79 |
| C51 | VSb 1.5 Sn .125 Ti .05 Fe .1 Ox + 20% SiO2 | 0.44 | 485 | 15 | 3.00 | 0.80 | 1.99 | 1.99 | 21.03 | 53.72 |
| C52 | VSb 1.8 Sn .04 Ti .02 Fe .5 Ox + 20% SiO2 | 1.59 | 480 | 15 | 3.00 | 0.81 | 2.00 | 1.99 | 20.09 | 53.67 |
| 53 | VSb 1.7 Ti 0.1 Fe 0.6 + 20% SiO2 | 1.34 | 480 | 16 | 3.00 | 0.80 | 2.00 | 1.98 | 20.10 | 53.60 |
| C54 | VSb 1.8 Sn 0.05 Ti 0.15 Fe 0.1 Ox + 20% SiO2 | 0.37 | 480 | 15 | 3.00 | 0.81 | 1.96 | 2.02 | 20.24 | 53.42 |
| C55 | VSb 1.5 Sn .125 Ti .05 Fe .1 Ox + 20% SiO2 | 0.44 | 488 | 15 | 3.00 | 0.80 | 1.99 | 1.99 | 21.36 | 53.28 |
| C56 | VSb 1.5 Sn 0.2 Ti 0.1 Fe 0.35 Ox + 20% SiO2 | 1.49 | 475 | 15 | 3.00 | 0.81 | 1.97 | 2.01 | 20.35 | 53.10 |
| 57 | VSb 1.5 Ti .15 Fe .4 Ox + 20% SiO2 | 1.08 | 475 | 15 | 3.00 | 0.79 | 2.01 | 2.00 | 20.71 | 52.76 |
| 58 | VSb 1.8 Sn .02 Ti .02 Fe .6 Ox + 20% SiO2 | 1.14 | 480 | 15 | 3.00 | 0.82 | 2.01 | 2.00 | 20.71 | 52.64 |
| C59 | VSb 1.8 Sn .35 Ti .05 Fe .6 Ox + 20% SiO2 | 2.32 | 480 | 15 | 3.00 | 0.79 | 2.00 | 2.01 | 19.85 | 51.27 |

While the invention has been described in conjunction with the specific embodiments thereof, it is evident that many alternatives, modifications and variations will be apparent to those skilled in the art in light of the foregoing description. Accordingly, it is intended to embrace all such alternatives, modifications and variations as fall within the spirit and scope of the appended claims.

What we claim as our invention is:

1. An ammoxidation catalyst characterized by the following empirical formula comprising:

$$VSb_aSn_bTi_cFe_dO_x$$

where $1 \leq a \leq 1.8$ $0 \leq b \leq 0.35$ $0 \leq c \leq 0.15$ $0 < d \leq 0.8$ $0 < b+c \leq 0.5$ $1 \leq a-d < 1.8$ and when $a-d > 1.2$ then $0 < d < 0.5$ and $0.3 \leq b+c \leq 0.5$ and when $a-d \leq 1.2$ then $0.2 < d \leq 0.8$ and $0 < b+c < 0.3$ and x is determined by the oxidation states of the cations present in the catalyst.

2. The catalyst of claim 1 wherein $1.3 \leq a \leq 1.8$.
3. The catalyst of claim 2 wherein $0.2 \leq d \leq 0.6$.
4. The catalyst of claim 3 wherein $1 \leq a-d \leq 1.2$.
5. The catalyst of claim 1 wherein $1.5 \leq a \leq 1.8$.
6. The catalyst of claim 3 wherein $0.3 \leq d \leq 0.6$.
7. The catalyst of claim 1 wherein the catalyst is calcined at a temperature of at least 780° C.
8. The catalyst of claim 2 wherein the catalyst is calcined at a temperature of at least 780° C.
9. The catalyst of claim 3 wherein the catalyst is calcined at a temperature of at least 780° C.
10. The catalyst of claim 4 wherein the catalyst is calcined at a temperature of at least 780° C.
11. The catalyst of claim 5 wherein the catalyst is calcined at a temperature of at least 780° C.
12. The catalyst of claim 6 wherein the catalyst is calcined at a temperature of at least 780° C.
13. An ammoxidation catalyst characterized by the following empirical formula comprising:

$$VSb_aSn_bTi_cFe_dO_x$$

where $1.3 \leq a \leq 1.8$ $0 \leq b \leq 0.2$ $0 \leq c \leq 0.1$ $0.2 < d \leq 0.6$ $0 < b+c < 0.3$ $1 \leq a-d \leq 1.2$ and x is determined by the oxidation states of the cations present in the catalyst.

14. The catalyst of claim 13 wherein the catalyst is calcined at a temperature of at least 780° C.

15. An ammoxidation catalyst characterized by the following empirical formula:

$$VSb_aSn_bTi_cFe_dO_x$$

where
$1.5 \leq a \leq 1.8$
$0 \leq b \leq 0.1$
$0 \leq c \leq 0.05$
$0.3 \leq d \leq 0.6$
$0 < b+c \leq 0.15$
$1 \leq a-d \leq 1.2$
and x is determined by the oxidation states of the cations present in the catalyst.

16. The catalyst of claim 15 wherein the catalyst is calcined at a temperature of at least 780° C.

UNITED STATES PATENT AND TRADEMARK OFFICE
CERTIFICATE OF CORRECTION

PATENT NO.: 5,994,259
DATED: November 30, 1999
INVENTOR(S): James Frank Brazdil, Jr., Joseph Peter Bartek It is certified that error appears in the above-identified patent and that said Letters Patent is hereby corrected as shown below:

IN TABLE III,
Example No. 17:   "Acrylonitrile
                   Selectivity
                      (%)
                   _____

55.14      "

should read:
                   "Acrylonitrile
                    Selectivity
                       (%)
                   _____

59.14      "

UNITED STATES PATENT AND TRADEMARK OFFICE
CERTIFICATE OF CORRECTION

PATENT NO.: 5,994,259

Page 2 of 3

DATED: November 30, 1999

INVENTOR(S): James Frank Brazdil, Jr., Joseph Peter Bartek

It is certified that error appears in the above-identified patent and that said Letters Patent is hereby corrected as shown below:

Patent reads:

Col.    Line

IN TABLE III,
Example No. 18:        "Catalyst Composition

VSb 1.5 Sn .05 Ti .15" (. . .)

should read:
                                        "Catalyst Composition

VSb 1.5 Sn .05 Ti .05" (. . .)

IN TABLE III,
Example No. 28:        "Catalyst Composition

VSb 1.5 Sn .2 Ti .5" (. . .)

should read:
                                        "Catalyst Composition

VSb 1.5 Sn .2 Ti .1" (. . .)

UNITED STATES PATENT AND TRADEMARK OFFICE
CERTIFICATE OF CORRECTION

PATENT NO.: 5,994,259

DATED: November 30, 1999

INVENTOR(S): James Frank Brazdil, Jr., Joseph Peter Bartek

It is certified that error appears in the above-identified patent and that said Letters Patent is hereby corrected as shown below:

Patent reads:

| Col. | Line |
|------|------|
| 5 | 66 |

"wherein $0.2 \leq d \leq 0.6$"

should read:
"wherein $0.2 < d \leq 0.6$"

Signed and Sealed this

Twenty-sixth Day of December, 2000

Attest:

Q. TODD DICKINSON

*Attesting Officer*          *Director of Patents and Trademarks*